United States Patent [19]

Gaudin

[11] Patent Number: 5,464,824
[45] Date of Patent: Nov. 7, 1995

[54] USE OF FURANONES AS PERFUMING INGREDIENTS

[75] Inventor: Jean-Marc Gaudin, Annemasse, France

[73] Assignee: Firmenich SA, Geneva, Switzerland

[21] Appl. No.: 256,219

[22] PCT Filed: Nov. 11, 1993

[86] PCT No.: PCT/EP93/03164

§ 371 Date: Jul. 5, 1994

§ 102(e) Date: Jul. 5, 1994

[87] PCT Pub. No.: WO94/12143

PCT Pub. Date: Jun. 9, 1994

[30] Foreign Application Priority Data

Nov. 18, 1992 [CH] Switzerland .............. 3533/92

[51] Int. Cl.[6] ........................ A61K 7/46
[52] U.S. Cl. ........................ 512/13; 549/302
[58] Field of Search .............. 549/302; 512/13

[56] References Cited

U.S. PATENT DOCUMENTS

| | | | |
|---|---|---|---|
| 3,850,963 | 11/1974 | Thoma et al. | 512/13 |
| 4,407,740 | 10/1983 | Kopsel et al. | 512/13 |
| 5,114,493 | 5/1992 | Podraza | 549/302 |
| 5,137,035 | 8/1992 | Podraza | 549/295 |

FOREIGN PATENT DOCUMENTS

| | | | |
|---|---|---|---|
| 0041122 | 12/1981 | European Pat. Off. | C11B 9/00 |
| 0167265 | 1/1986 | European Pat. Off. | A01N 43/22 |
| 0219199 | 4/1987 | European Pat. Off. | C07D 311/76 |
| 1184774 | 1/1965 | Germany | 549/302 |

OTHER PUBLICATIONS

Database WPI, Section Ch, Week 8213, Derwent Publications Ltd., London, GB; Class D18, AN 82-24625E & JP, A, 57 029 279 (Japan Tobacco & Salt), Feb. 17, 1982.
Agricultural and Biological Chemistry, vol. 37, No. 10, 1973, Tokyo, JP, pp. 2441–2442, I. Sakata et al., "Isolation and Identification of 2,3-Dimethyl-4-hydroxy-2-nonenoic Acid Lactone from Shubi".
Food Technologists, vol. 44, No. 2, Feb. 1990, Chicago, U.S., G. A. Burdock et al., "15. GRAS Substances", pp. 78, 80, 83, 84, 86.
Journal of the American Chemical Society, vol. 111, 1989, Washington, D.C., U.S., pp. 5472–5474, E. J. Corey et al., "Enantiospecific Total Synthesis of Pseudopterosins A and E".
Tetrahedron Letters, vol. 32, No. 38, 1991, Oxford, GB, pp. 5191–5192, M. Carda et al., "Total Synthesis of (−)—Mintlactone".
Chemical and Pharmaceutical Bulletin, vol. 31, No. 8, 1983, Tokyo, JP, pp. 2639–2651, I. Kitagawa et al., "Chemical Transformation of Terpenoids. V. Acidic Conversions of 10—Hydroxygeraniol and 10—Hydroxynerol Derivatives Leading to Cyclic Monoterpenoids".
Journal of Organic Chemisty, vol. 47, 1982, Easton, U.S., pp. 741–743, Y. Ito et al., "A New Approach for Stereoselective Synthesis of Gama-Butyrolactones".

*Primary Examiner*—James H. Reamer
*Attorney, Agent, or Firm*—Pennie & Edmonds

[57] ABSTRACT

The furanones of formula

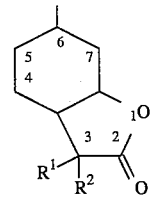

(I)

wherein symbols $R^1$ and $R^2$, taken separately, are identical and represent each a methyl radical, or are different and represent each a hydrogen atom or a methyl radical, or, taken together, represent a methylene radical, are useful as perfuming ingredients for the preparation of perfuming compositions and perfumed articles, to which they impart odors of the coumarinic and balsamic type.

20 Claims, No Drawings

USE OF FURANONES AS PERFUMING INGREDIENTS

This application is a 371 of PCT/EP93/03164, Nov. 11, 1993.

TECHNICAL FIELD

The present invention relates to the perfume industry. More particularly, it concerns the use of a furanone of formula

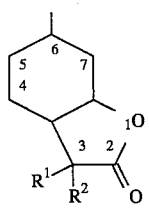

(I)

wherein symbols $R^1$ and $R^2$, taken separately, are identical and represent each a methyl radical, or are different and represent each a hydrogen atom or a methyl radical, or, taken together, represent a methylene radical.

PRIOR ART

Formula (I) furanones are homologues of 5,6,7,7a-tetrahydro-7a-methoxy- 3,6-dimethyl-2(4H)-benzo[b]furanone, also known under the name of mintlactone, a natural component of peppermint essential oil, and the use of which in perfumery and the flavor industry is described in the prior art [see U.S. Pat. No. 4,407,740].

On the other hand, U.S. Pat. No. 5,114,493 describes the use of lactones of formula

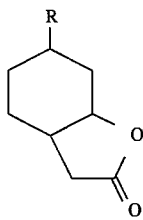

wherein R is a $C_1$ a $C_6$ alkyl radical, a $C_1$-$C_4$ alkylphenyl radical or a $C_1$-$C_4$ alkoxyphenyl radical, for flavoring tobacco.

The structures of furanones (I) are also known from the prior art. For example, the synthesis of perhydro-6-methyl-3-methylene-2-benzo[b]furanone has been the object of several publications [see, for example, J. M. Fang et al., Proc. Nat. Sci. Counc. ROC(A) 9, 95 (1985)], while perhydro-3,6-dimethyl-2-benzo[b]furanone was described in European patent EP 219 199, relating to a process for the preparation of lactones. Although this patent makes no reference to any particular properties of this furanone, the use of this compound as an insect repellent is known—see European patent application EP 167 265-.

The synthesis of perhydro-3,3,6-trimethyl-2-benzo[b]furanone has also been described by I. Yoshihiko et al. in J. Org. Chem. 47, 741 (1982).

On the other hand, several optically active isomers of compounds (I), the structure of which comprises several chiral centers, have been described in the literature, their characterization being however often deficient [see, for example, J. M. Fang et al., cited ref.; M. Carda et al., Tetrahedron Lett. 32, 5191 (1991); I. Kitagawa et al., Chem. Pharm. Bull. 31, 2639 (1983); E. J. Corey et al., J. Am. Chem. Soc. 111, 5472 (1989); C. W. Jefford et al., J. Chem. Soc. Chem. Comm. 1988, 634].

Despite the abundance of synthetical and structural descriptions, and the chemical similarity between furanones (I) and their homologues known from U.S. Pat. Nos. 4,407,740 and 5,114,493, to our knowledge the odor properties of these furanones (I) have gone unnoticed heretofore. We have been unable to find in the cited prior art any reference, or even suggestion, of the eventual usefulness of these furanones, or of any isomer thereof, as perfuming ingredients.

DESCRIPTION OF THE INVENTION

We have now discovered that these compounds possess surprising odor properties in view of the prior art, which render their use in perfumery very advantageous.

For example, perhydro-6-methyl-3-methylene-2-benzo[b]furanone possesses a very powerful odor of the coumarinic, fat, lactonic type, with a balsamic bottom note reminiscent of the odor of daffodil. This is an odor note which is very dose to that of coumarine and which is best represented in (+)-( 3aS,6R,7aR)-perhydro-6-methyl-3-methylene-2-benzo[b ]furanone, a preferred compound of the invention.

As for perhydro-3,6-dimethyl-2-benzo[b]furanone, it possesses a very powerful coumarine type note, with a hay-like aspect which is reminiscent of the odor of flouve and Florex®[5 and 6-ethylideneoctahydro-5,8 -methane-2H-1-benzopyran-2-one; origin: Firmenich SA, Geneva, Switzerland], as well as a fruity-balsamic undernote reminiscent of the odor of tonka and liquorice.

We have discovered unexpectedly that the odor of this compound is particularly useful since, according to the perfumers, it is olfactively the closest note to that of coumarine known to this day. This is dearly seen from the comparaison examples presented further on, wherein this furanone is evaluated against the compounds presently available on the market and whose odors are related to that of coumarine.

The odor properties of furanones (I) appear as totally surprising in view of the prior art. In fact, their odor is totally distinct, both qualitatively and quantitatively, from that of their known homologue mentioned above, i.e. mintlactone. As the comparaison examples presented further on show, the latter possesses a very powerful odor note, the strength of which is several orders of magnitude inferior to that of the above-mentioned furanones (I). Its note is less coumarinic and more lactonic than that of the latter, and it does not possess the hay-like character which is typical of coumarine and which is also found in the odor of furanones (I), particularly in that of perhydro-3,6- dimethyl-2-benzo[b] furanone. Furthermore, the latter also possesses a fresh-aromatic note, reminiscent of laevo-carvone, which note is totally absent from the odor of mintlactone, which has a much fruitier odor.

On the other hand, mintlactone is not at all substantive, unlike furanones (I). This dearly springs up from the substantivity comparaison test presented further on.

It has also been discovered unexpectedly that the numerous optically active isomers of perhydro-3,6-dimethyl-2-benzo[b]furanone all possess, in a more or less marked way, the desired coumarinic note, together with a variety of other olfactive nuances which render all these compounds useful for the preparation of perfuming compositions and perfumed articles.

Amongst said isomers, one can cite as preferred compounds (+)-( 3R,3aS,6R,7aR)-perhydro-3,6-dimethyl-2-benzo[b]furanone and (+)-( 3S,3aS,6R,7aR)-perhydro-3,6-dimethyl-2-benzo[b]furanone. These two compounds possess very powerful coumarinic odor notes, the odor of the former being less lactonic but sweeter than that of the latter, with a caramel type character. The odor of the second compound cited in which the above-mentioned tonka, beans, hay, flouve type characters are best represented, is also more coumarinic and powerful than that of the first, whose coumarinic character is more marked in the bottom note than in the top note, and is accompanied of a metallic side. Perfuming mixtures which have a predominant amount of one or the other of these compounds have also been judged as very useful perfuming ingredients according to the invention.

Furthermore, we were surprised to observe that mixtures of the optically active isomers could sometimes have comparable, if not better, odor performances than their individual ingredients and turn out to be choice fragrance ingredients. We particularly observed an exhalting effect of the odor properties of the two above-cited preferred compounds of the invention whenever these compounds were admixed together, or when their mixture was used in combination with other isomers in compositions containing predominant amounts of said mixture of (+)-(3R,3aS,6R,7aR)-perhydro-3,6-dimethyl- 2-benzo[b]furanone and (+)-(3S,3aS,6R,7aR)-perhydro-3,6-dimethyl- 2-benzo[b]furanone. Said compositions, having 50% or more of said mixture, possessed the above-mentioned odor notes typical of perhydro-3,6-dimethyl 2-benzo[b]furanone, but their odor appeared as more powerful and richer in the desired coumarinic and lactonic character than the odor of the individual isomers which formed the mixture. These are novel compositions, which possess unexpected properties in view of the prior art, and are thus also an object of the invention.

In addition, when such mixtures are directly obtained from certain synthetic methods, they present the further advantage of being more economical than the pure optically active forms, the synthesis of which is more costly.

Among the isomers of perhydro-3,6-dimethyl-2-benzo[b]furanone, one can yet cite as a preferred compound (−)-(3S, 3aR,6R,7aS)-perhydro-3,6-dimethyl- 2-benzo[b]furanone which possesses a coumarinic, flouve, hay, vaguely sulphury odor.

Whenever there is a reference to perhydro-3,6-dimethyl-2-benzo[ b]furanone in the application examples, this is meant to refer both to the racemic mixture and to any of the optically active isomers, namely to those which are preferred according to the invention, or yet to the compositions which contain at least 50% by weight of one of the (+)-(3R,3aS, 6R,7aR) and (+)-(3S,3aS,6R,7aR) isomers, or of their mixture.

As a result of their odor properties, furanones (I), their optically active isomers, as well as the mixtures of said isomers, are perfuming ingredients which are equally convenient for technical and fine perfumery applications. They are adapted to the preparation of perfuming bases and compositions, perfumes and colognes, as well as to perfuming a variety of consumer articles such as soaps, bath and shower gels, shampoos and other hair-care products, body or air deodorants, and cosmetic preparations. Since their odor note is very tenacious, they can be advantageously used to perfume detergents and fabric softeners. They also find convenient use in household products.

In such applications, they can be used on their own or, as is more common in the art, in admixture with other perfuming ingredients, solvents or adjuvants of current use in perfumery.

The concentrations in which they can be used depend on the flagrance effect that is desired to achieve, as well as on the nature of the coingredients with which they are admixed in the perfuming compositions and perfuming articles containing them. Such concentrations can therefore vary in a wide range of values. By way of example, one can cite concentrations of the order of 1 to 10%, or even 20% or more, by weight, relative to the weight of the composition into which they are incorporated, upon their use for the preparation of perfuming bases and compositions. Much lower concentrations values than these will generally be used when employing these compounds for perfuming the various consumer articles cited above.

EMBODIMENTS OF THE INVENTION

Compounds (I) are prepared from products of commercial origin or which can be easily prepared according to known methods. The following schematic diagrams illustrate the methods used in each particular case.

SCHEME I

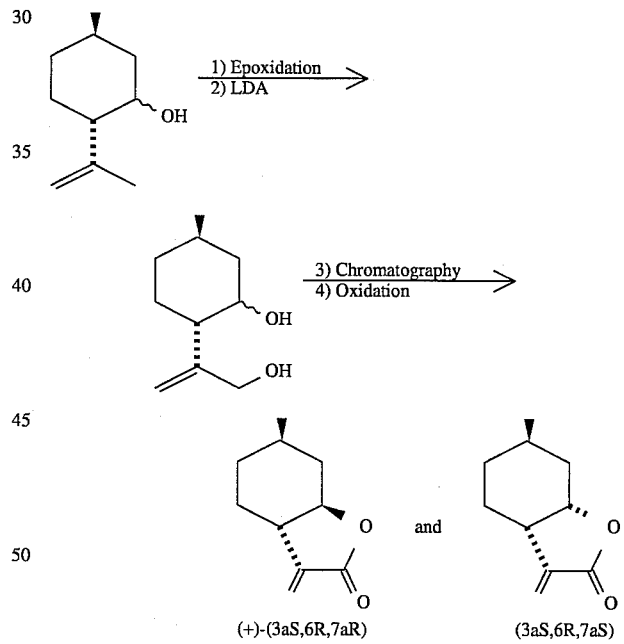

The starting product (Fluka) in this scheme is a mixture of (−)-isopulegol (72%) and (+)-neoisopulegol (20%). The epoxidation of this mixture by means of metachloroperbenzoic acid in dichloromethane [see T. -L. Ho et al., Synth. Comm. 19, 813 (1989) and T. G. Waddell et al., J. Org. Chem. 52, 4802 (1987) for analogous reactions] and treatment with 2.5 eq. of lithium diisopropylamine (LDA) in THF [see, for example, K. -H. Schulte-Elte, Helv. Chim. Acta 50, 153 (1967) for analogous reactions] provide a mixture of the diols indicated, which can then be separated via preparative chromatography and oxidized by means of silver oxide to give the two lactones indicated, in a pure state.

Other methods of preparation of these two lactones are described for example by S. B. Balkrishna et al., Heterocycles 16, 2091 (1981) and T. J. Brocksom et al., Synth. Comm. 18, 1403 (1988).

When starting from pure (–)-isopulégol (Fluka) and subjecting the intermediate diol to catalytic hydrogenation, as illustrated in the following scheme:

by means of potassium permanganate [see C. W. Jefford et al., J. Chem. Soc., Chem. Comm. 1988, 634] to provide the two lactones indicated in a pure state.

Scheme III hereafter illustrates the preparation of the other two isomers of perhydro-3,6-dimethyl-2-benzo[b]furanone, starting from pure (+)-neoisopulegol (obtained by chromatographic separation of the technical mixture cited in Scheme I), via hydroboration of the latter in THF [process analogous to that described by K. -H. Schulte-Elte, cited reference], followed by oxidation of the obtained mixture of diols.

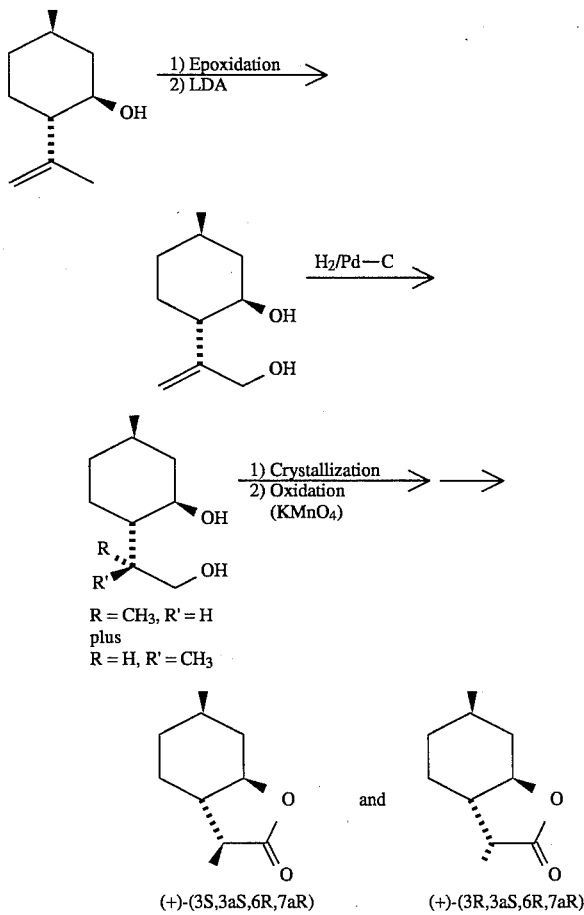

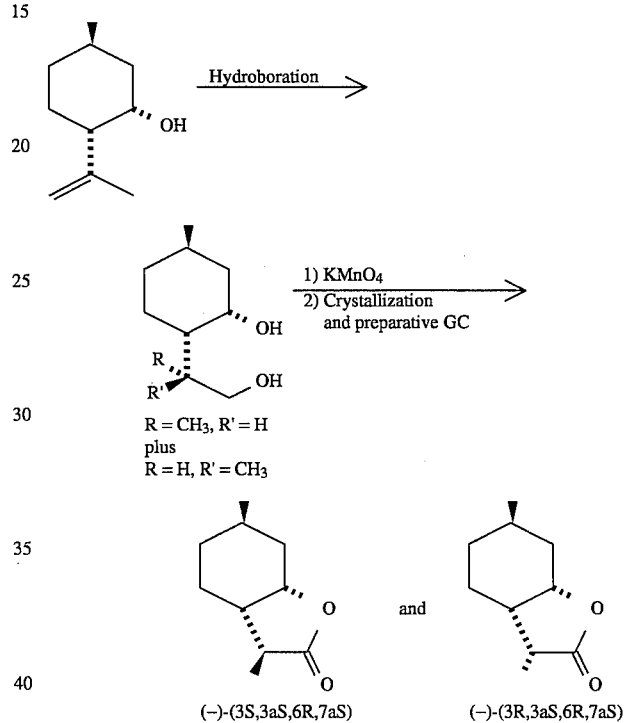

There is obtained a mixture of the indicated diols. These are separated via crystallization from hexane and then oxidized One obtains a mixture of the two desired lactones, separates the major isomer by crystallization from hexane, and the minor isomer by preparative gas chromatography of the mother liquours.

As illustrated in Scheme IV hereafter,

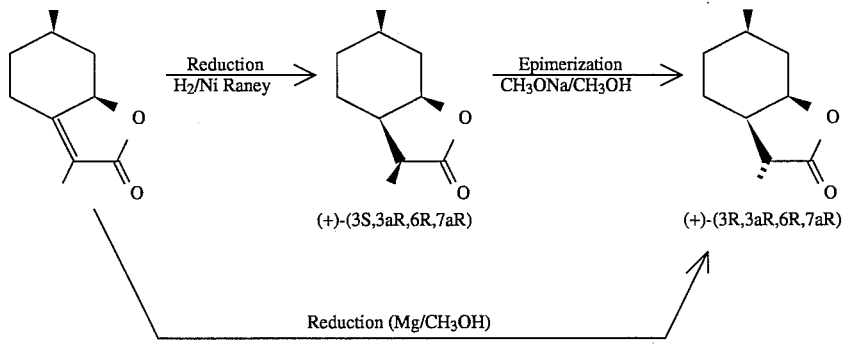

catalytic reduction of (−)-mintlactone provides the lactone having configuration (3S,3aR,6R,7aR), while reduction of the same starting product by means of magnesium in methanol [see T. Hudlicky et al., Tetrahedron Let. 28, 5287 (1987) and H. Yoda et al., Chem. Let. 1989, 1391, for analogous reactions] provides the lactone of configuration (3R,3aR,6R,7aR). The latter can also be obtained by epimerization of its indicated epimer, by means of sodium methylate.

Reduction of the (+)-(3S,3aR,6R,7aR)-perhydro-3,6-dimethyl-2-benzo[b] furanone prepared above by means of LiAlH₄ in diethylether provided the diol indicated in the following Scheme V:

SCHEME V

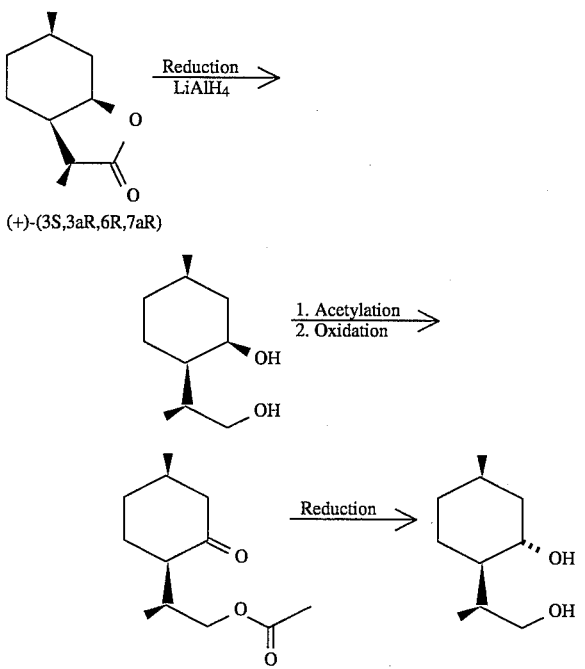

(+)-(3S,3aR,6R,7aR)

Acetylation of this diol with one equivalent of acetic anhydride in pyridine, followed by oxidation with Jones reagent, provided the intermediate ketone, the reduction of which made it possible to obtain the diol indicated. This diol possessed the appropriate configuration to provide, via oxidation with potassium permanganate, the lactone of configuration (3S,3aR,6R,7aS), as indicated in scheme VI:

SCHEME VI

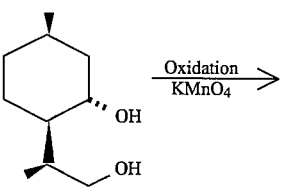

-continued
SCHEME VI

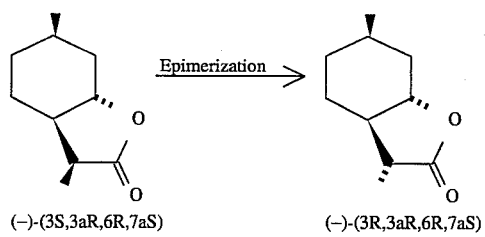

(−)-(3S,3aR,6R,7aS)    (−)-(3R,3aR,6R,7aS)

Epimerization of this lactone under basic conditions (CH₃ONa/THF) provided its epimer indicated above.

All the lactones (I) whose preparation is described above possess a methyl group of R configuration in position 6. The use of the appropriate starting products, having the said methyl group in a configuration which is enantiomeric to that indicated in the schemes above, made it possible to obtain the corresponding 6S configuration lactones (I), of course.

Compounds (I) thus obtained were exhaustively characterised by means of spectroscopic techniques (MS, NMR-COSY, nOe, etc ...) and their analytical data are presented further on.

When mixtures of optically active isomers were used as starting products, there were obviously obtained the corresponding mixtures lactones (I), which proved to be excellent perfuming ingredients. For example, when applying to the technical mixture of (−)-isopulegol and (+)-neoisopulegol cited in Scheme I, the reaction sequence described in Scheme II, excepting the diol separation via crystallization, there was obtained a mixture of lactones which contained about 50% by weight of (+)-(3S,3aS,6R,7aR)- perhydro-3, 6-dimethyl-2-benzo[b]furanone, 30% by weight of (+)-( 3R,3aS,6R,7aR)-perhydro-3,6-dimethyl-2-benzo[b]furanone, 11% by weight of (−)-(3S,3aS,6R,7aS)-perhydro-3,6-dimethyl-2-benzo[b]furanone and 7% by weight of (−)-(3R, 3aS,6R,7aS)-perhydro-3,6-dimethyl-2-benzo[b]furanone.

This mixture possessed such good odor properties that it turned out to be a preferred perfuming ingredient according to the invention. Moreover, said mixture was also useful as starting product in the synthesis of (−)-(3aS,6R,7aS)-perhydro- 3,3,6-trimethyl-2-benzo[b]furanone, described further on.

Other mixtures were obtained from the same technical quality isopulegol as starting product, but varying slightly the reaction conditions. For example, hydroboration of this starting product, followed by oxidation with KMnO₄, in an analogous way to that illustrated in Scheme III, provided a mixture containing around 13% by weight of (+)-(3S,3aS, 6R,7aR)-perhydro- 3,6-dimethyl-2-benzo[b]furanone, 61% by weight of (+)-(3R,3aS,6R,7aR)-perhydro- 3,6-dimethyl-2-benzo[b]furanone, 20% by weight of (−)-( 3S,3aS,6R, 7aS)-perhydro-3,6-dimethyl-2-benzo[b]furanone and 6% by weight of (−)-(3R,3aS,6R,7aS)-perhydro-3,6-dimethyl-2-benzo[b]furanone which also revealed itself as a useful perfuming ingredient.

These mixtures containing a predominant amount of the two preferred isomers of perhydro-3,6-dimethyl-2-benzo[b] furanone, i.e. (+)-(3S,3aS,6R,7aR) and (+)-(3R,3aS,6R, 7aR), developped in fact very powerful coumarinic odors, with the typical hay, flouve characters already mentioned above.

Concerning the racemic products (I), they can be prepared by the methods described in the above-cited prior art, or yet according to the methods described for example in Schemes I and II, but using racemic starting products.

The methods of preparation of compounds (I) are described in detail hereinafter.

A. Preparation of (+)-(3S,3aS,6R,7aR)-perhydro-3,6-dimethyl-2-benzo[b] furanone and of (+)-(3R,3aS,6R,7aR)-perhydro-3,6-dimethyl-2-benzo[b] furanone To 40.7 g (264 mmole) of (−)-(1R,3R,4S)-8-p-menthen-3-ol ($[\alpha]_D^{20}$=−7.74°) in dichloromethane (130 ml) there were added 64.5 g (317 mmole) of m-chloroperbenzoic acid. The mixture was stirred during 4 h at room temperature, then filtered, washed with $NaHCO_3$, water and brine. The organic phase was dried and concentrated, and the raw product was distilled. A solution of 16.15 g (95 mmole) of the thus distilled product in THF (30 ml) was slowly added, at 0° C., to 295 mmole of LDA in THF (170 ml). The mixture was heated to 45° C. for 1 h and then cooled to room temperature. The reaction mixture was poured on ice and extracted with ether. The organic phase was washed with brine, dried and concentrated to give 14 g of raw product. The latter was recrystallized from hexane to give 11.96 g of (1R,3R,4S)-8(10)-p-menthene-3,9-diol in a pure state.

15G (88 mmole) of this diol were hydrogenated with 0.15 g of 10% Pd/C, in ethyl acetate (150 ml), at atmospheric pressure of $H_2$. The raw product (15.7 g) was distilled to give 10.6 g (yield 70%) of a mixture of (1R,3R,4S,8S)-3,9-p-menthanediol and (1R,3R,4S,8R)-3,9-p-menthanediol. These two diols were then separated by crystallization from hexane.

(1R, 3R, 4S, 8S)-3,9-p-menthanediol
NMR($^1$H, 360MHz, $CDCl_3$): 0.85(d, J=7Hz, 3H); 0.89(m, 1H); 0.92(d, J=6Hz, 3H); 0.98(m, 2H); 1.35(m, 1H); 1.41(m, 1H); 1.63(m, 2H); 1.99(dxm, J=13Hz, 1H); 2.07(m, 1H); 3.42(dxdxd, $J_1$=11, $J_2$=4, $J_3$=4Hz, 1H); 3.48(dxd, $J_1$=11, $J_2$=7Hz, 1H); 3.56(dxd, $J_1$=11, $J_2$=5Hz, 1H) δppm.
NMR($^{13}$C, 360MHz, $CDCl_3$): 12.6(q); 22.2(q); 25.3(t); 31.6(d); 34.4(t); 35.6(d); 45.2(d); 45.6(d); 66.6(t); 71.7(d) δppm.
MS: 172(1, M$^+$), 154(3), 139(6), 123(16), 112(16), 95(38), 81(100), 71(63), 55(57), 41(32).

(−)-(1R, 3R, 4S, 8R)-3,9-p-menthanediol
$[\alpha]_D^{20}$ =−22.5°; c=1.2%, in $CHCl_3$
M.p. 100°–101° C.
NMR($^1$H, 360MHz, $CDCl_3$): 0.93(d, J=7Hz, 3H); 0.97(d, J=7Hz, 3H); 0.8–1.0(m, 2H); 1.24(dxdxdxd, $J_1$=11, $J_2$=11, $J_3$=11, $J_4$=3Hz, 1H); 1.35(dxm, J=11Hz, 1H); 1.42(m, 1H); 1.56(dxm, J=13Hz, 1H); 1.64(dxm, J=13Hz, 1H); 1.84(m, 1H); 1.97(dxm, J=13Hz, 1H); 3.44(dxdxd, $J_1$=10, $J_2$=10, $J_3$=4Hz, 1H); 3.58 (dxd, $J_1$=11, $J_2$=3Hz, 1H); 3.65(dxd, $J_1$=11, $J_2$=5Hz, 1H) δppm.
NMR($^{13}$C, 360MHz, $CDCl_3$): 12.0(q); 22.1(q); 29.5(t); 31.5(d); 34.7(t); 38.6(d); 44.6(0; 48.6(d); 67.0(t); 70.1 (d) δppm.
MS: 172(1, M$^+$), 154(3), 139(7), 124(18), 112(28), 95(33), 81(100), 71(62), 55(65), 41 (35).

These two diols were then separately oxidized by means of potassium permanganate, in an analogous way to that described under B hereinafter, to give the desired lactones in a pure state.

(+)-(3R, 3aS, 6R, 7aR)-perhydro-3,6-dimethyl-2-benzo[b] furanone
(94% pure)
$[\alpha]_D^{20}$=+85.0°;c=0.7%, in $CHCl_3$
IR: 2940, 2883, 1808, 1158, 962 cm$^{-1}$
NMR($^1$H, 360MHz, CDCl3): 1.02(d, J=7Hz, 3H); 1.11(m, 1H); 1.15(d, J=7Hz, 3H); 1.24(dxdxd, $J_1$=11, $J_2$=11, $J_3$=11Hz, 1H); 1.34(m, 1H); 1.60(m, 1H); 1.77(m, 1H); 1.82(m, 1H); 1.93(m, 1H); 2.25(dxdxd, $J_1$=11, $J_2$=4, $J_3$=4Hz, 1H); 2.64(dxq, $J_1$=7, $J_2$=7Hz, 1H); 4.00(dxdxd, $J_1$=11, $J_2$=11, $J_3$=4Hz, 1H) δd ppm.
NMR($^{13}$C, 360MHz, $CDCl_3$): 9.6(q); 22.0(q); 23.8(t); 31.3(d); 34.2(t); 38.8(t); 38.8(d); 47.2(d); 81.5(d); 180.4(s) δppm.
MS: 167(1), 139(1), 124(4), 109(18), 95(27), 81(100), 67(73), 55(24), 41(30).
Odor: described in the introduction.

(+)-(3S, 3aS, 6R, 7aR)-perhydro-3,6-dimethyl-2-benzo[b] furanone
(97% pure)
$[\alpha]_D^{20}$=+19.5°;c =1.25%, in $CHCl_3$
IR: 2939, 2884, 1809, 1175, 1093, 1006 cm$^{-1}$
NMR($^1$H, 360MHz, $CDCl_3$): 1.02(d, J=7Hz, 3H); 1.03(m, 1H); 1.22(d, J=7Hz, 3H); 1.22(m, 1H); 1.26(m, 1H); 1.47(dxdxdxd, $J_1$=13, $J_2$=13, $J_3$=13, $J_4$=4Hz, 1H); 1.63(m, 1H); 1.82(dxm, $J_1$=13Hz, 1H); 1.94(dxdxd, $J_1$=13, $J_2$=5, $J_3$=3Hz, 1H); 2.22(m, 1H); 2.24(m, 1H); 3.76(dxdxd, $J_1$=13, $J_2$=13, $J_3$=4Hz, 1H) δppm.
NMR($^{13}$C, 360MHz, $CDCl_3$): 12.6(q); 22.0(q); 26.7(t); 31.4(d); 34.2(t); 38.2(t); 41.4(d); 51.5(d); 82.5(d); 179.5(s) δppm.
MS: 167(1), 139(1), 124(6), 109(16), 95(27), 81(100), 67(62), 55(18), 41(17).
Odor: described in the introduction.

B. Preparation of (−)-(3S,3aS,6R,7aS)-perhydro-3,6-dimethyl-2-benzo[b] furanone and of (−)-(3R,3aS,6R,7aS)-perhydro-3,6-dimethyl-2-benzo[b] furanone To a cooled solution of (+)-(1R,3S,4S)-8-p-menthen-3-ol ($[\alpha]_D^{20}$=+9.75°; 30.8 g; 200 mmole) and sodium borohydride (4.18 g; 110 mmole) in THF (80 ml), maintained under nitrogen, there was added dropwise, over 1 h, at a temperature comprised between −10° and 0° C., 21.3 g (150 mmole) of boron trifluoride ethyl etherate. Once the addition had been completed, the mixture was stirred for 3 h at 0° C. 30 Ml of water were then added slowly (15 min) and the mixture was stirred for a further 15 min. Still at 0° C., there were added 80 g of a 12% KOH solution in ethanol, followed, 20 min later, of 22 g (460 mmole) of hydrogen peroxide (70% solution in water). Once the addition had been completed, the reaction mixture was stirred at 20° C. for another 2 h. THF was stripped, the raw product extracted with ether and washed with brine. The organic mixture was dried and concentrated to give 32 g of a raw oil consisting of a mixture of diols (1R,3S,4S,8S)-3,9-p-menthanediol and (1R,3S,4S,8R)-3,9-p-menthanediol.

This mixture of diols was then oxidized as follows: 6.88 g (40 mmole) of this oil, in solution in 20 ml of ethyl acetate, were added dropwise over 10 min to 15.15 g (96 mmole) of potassium permanganate in 50 ml of ethyl acetate. The mixture was stirred overnight at room temperature and then hydrolized by adding a saturated solution of sodium bisulfite until complete discoloring. The white precipitate was filtered and the organic phase washed with brine to bring its pH to 7, dried and concentrated to give 6d34 g of a mixture of the desired lactones. (−)-( 3R,3aS,6R,7aS)-perhydro-3,6-dimethyl-2-benzo[b]furanone was obtained from this mixture by recrystallization from hexane, while (−)-( 3S,3aS, 6R,7aS)-perhydro-3,6-dimethyl-2-benzo[b]furanone was isolated from the mother liquors by preparative gas chromatography. (−)-(3S, 3aS, 6R, 7aS)-perhydro-3,6-dimethyl-2-benxo[b]furanone
(98% pure)
$[\alpha]_D^{20}$= −67.9°; c=1.07%, in $CHCl_3$
M.p. 52–53° C.
IR: 2937, 1804, 1161, 969 cm$^{-1}$ NMR($^1$H, 360MHz, CDCl$_3$):0.93(d, J=7Hz, 3H); 0.94(m, 1H); 1.25(m, 2H); 1.27(d, J=7Hz, 3H); 1.80(m, 3H); 1.95(m, 1H); 2.17(dxm, J$_1$=14Hz, 1H); 2.36(q, J=7Hz, 1H); 4.69(dxd, J$_1$=4, J$_2$=4Hz, 1H) δppm.
NMR($^{13}$C, 360MHz, CDCl$_3$): 14.1(q); 21.5(q); 26.0(d); 27.3(t); 31.6(t); 36.0(t); 41.3(d); 44.1(d); 77.4(d); 180.5(s) δppm.
MS: 167(1), 139(1), 124(13), 109(19), 95(100), 81(55), 67(72), 55(30), 41(38).
Odor: coumarinic, lactonic, cold tobacco side.
(−)-(3R, 3aS, 6R, 7aS)-perhydro-3,6-dimethyl-2-benxo[b] furanone
(88% pure)
[α]$_D^{20}$=−31.3°;c=0.95%, in CHCl$_3$
M.p. 47–48° C.
IR: 2938, 1806, 1158, 962 cm$^{-1}$
NMR($^1$H, 360MHz, CDCl$_3$): 0.90(m, 1H); 0.92(d, J=7Hz, 3H); 1.11(m, 1H); 1.16(d, J=7Hz, 3H); 1.21 (m, 1H); 1.57(m, 1H); 1.67(m, 2H); 2.22(m, 2H); 2.79(dxq, J$_1$=7, J$_2$=7Hz, 1H); 4.44(m, 1H) δppm.
NMR($^{13}$C, 360MHz, CDCl$_3$): 9.1(q); 22.0(q); 23.2(t); 26.2(d); 32.1(t); 36.2(t); 39.1 (t); 42.3(d); 78.2(d); 179.8(s) δppm.
MS: 167(1), 139(1), 124(12), 109(18), 95(100), 81(38), 67(70), 55(27), 41(35).
Odor: coumarinic, fat.

C. Preparation of (+)-(3R,3aR,6R,7aR)-perhydro-3,6-dimethyl-2-benzo[b] furanone 1.70G (70 mmole) of magnesium were added, portionwise, to a solution of (−)-(6R,7aR)-5,6,7,7a-tetrahydro-3,6-dimethyl-2(4H)-benzo[b]furanone (0.83 g; 5 mmole) in THF (50 ml). The exothermic reaction was kept at a temperature dose to r. t. by means of water bath, overnight. The reaction mixture was hydrolized with a 10% HCl solution and extracted with ether. The organic phase was washed with brine, dried and concentrated. Flash chromatography purification gave 743 mg (yield 88%) of the title furanone, 99% pure.
[α]$_D^{20}$=+45.7°;c=0.9%, in CHCl$_3$
IR: 2939, 1802, 1169, 1007 cm$^{-1}$
NMR($^1$H, 360MHz, CDCl$_3$): 0.96(d, J=7Hz, 3H); 0.98(m, 2H); 1.21(d, J=7Hz, 3H); 1.40(m, 1H); 1.56(dxm, J$_1$=13Hz, 1H); 1.67(m, 1H); 1.86(dxm, J$_1$=14Hz, 1H); 2.08(m, 1H); 2.22(m, 1H); 2.48(dxq, J$_1$=14, J$_2$=7Hz, 1H); 4.49(dxdx, J$_1$=12, J$_2$=7, J$_3$=7Hz, 1H) δppm
NMR($^{13}$C, 360MHz, CDCl$_3$): 13.3(q); 22.0(q); 24.0(t); 28.7(t); 29.5(d); 35.3(d); 37.8(t); 41.7(d); 77.5(d); 179.6(s) δppm.
MS: 169(1), 139(1), 124(3), 109(19), 95(44), 81(100),67(65), 55(27), 41(32).

D. Preparation of (+)-(3S,3aR,6R,7aR)-perhydro-3,6-dimethyl-2-benzo[b] furanone 10G (60 mmole) of (−)-(6R,7aR)-5,6,7a-tetrahydro-3,6-dimethyl-2(4H)-benzo[b]furanone in methanol (40 ml) were hydrogenated with Raney Ni (3 g), under 50 atmospheres of H$_2$, over 3 days, at room temperature. Extraction of the reaction product with ether gave 9.7 g (yield 96%) of the desired furanone, which was purified to give a 98% pure product.
[α]$_D^{20}$=+9.2°; c=1.1%, in CHCl$_3$
IR: 2943, 1803, 1156, 972 cm$^{-1}$
NMR($^1$H, 360MHz, CDCl$_3$): 1.02(d, J=7Hz, 3H); 1.18(d, J=7Hz, 3H); 1.33(m, 1H); 1.50(m, 3H); 1.89(m, 3H); 2.32(m, 1H); 2.77(dxq, J$_1$=7, J$_2$=7Hz, 1H); 4.52(dxd, J$_1$=5, J$_2$=5Hz, 1H) δppm.
NMR($^{13}$C, 360MHz, CDCl$_3$): 9.7(q); 17.4(t); 19.8(q); 25.3(t); 28.9(t); 33.1(t); 38.8(d); 41.3(d); 77.9(d); 179.7(s) δppm.
MS: 167(1), 139(1), 124(10), 109(21), 95(100), 81(55), 67(76), 55(35), 41(44).
Odor: lactonic.

E. Preparation of (−)-(3S,3aR,6R,7aS)-perhydro-3,6-dimethyl-2-benzo[b] furanone 9.7 G (57.7 mmole) of (+)-(3S,3aR,6R,7aR)-perhydro-3,6-dimethyl-2-benzo[ b]furanone (prepared under D) were added slowly to 2.2 g (57 mmole) of LiAlH$_4$ in ether (200 ml). The exothermic reaction was kept at a temperature around 0° C. with an ice bath. Once the reaction had been completed, the mixture was diluted with ether and hydrolized with a small amount of brine. The white granular solid was extracted by filtering and washed with ether. The organic phase was filtered and evaporated to give 7.5 g (yield 76%) of (1R,3R,4R, 8S)-3,9-p-menthanediol, having the following analytical characteristics:
NMR($^1$H, 360MHz, CDCl$_3$): 0.89(m, 2H); 0.95(d, J=7Hz, 3H); 1.15(d, J=7Hz, 3H); 1.30(dxdxd, J$_1$=13, J$_2$=9, J$_3$=4Hz, 1H); 1.44(m, 1H); 1.53(m, 1H); 1.68(m, 2H); 1.85(m, 2H); 3.40(dxd, J$_1$=8, J$_2$=4Hz, 1H); 3.50(dxd, J$_1$=11, J$_2$8Hz, 1H); 3.94(m, 1H) δppm.
NMR($^{13}$C, 360MHz, CDCl$_3$): 17.3(t); 17.6(q); 21.4(q); 27.4(d); 32.1(t); 38.5(d); 39.1 (t); 46.4(d); 64.7(t); 71.3(d) δppm.
MS: 172(1, M$^+$), 154(4), 139(8), 123(28), 112(32), 95(69), 81(100), 71(80), 55(73), 41 (44).

To a solution of the diol prepared above (8 g; 46.7 mmole) in pyridine (50 ml) there were added, at −5° C., 4.8 g acetic anhydride. The reaction mixture was then stirred overnight at room temperature. After extracting with ether, the ethereal phase was washed with a 10% solution of HCl, water and brine. The product was dried over magnesium sulfate and concentrated. The mixture was subjected to flash chromatography (eluting agent: pentane/ether = 5/1) to give 7.8 g (yield 78%) of (1R,3R,4R,8S)-3-hydroxy-9-p-menthanyl acetate, with the following analytical characteristics:
NMR($^1$H, 360MHz, CDCl$_3$): 1.27(d, J=7Hz, 3H); 1.30(d, J=7Hz, 3H); 1.40(m, 3H); 1.50(m, 1H); 1.55–1.75(m, 3H); 1.82(m, 1H); 1.91(m, 1H); 2.07(s, 3H); 3.94(dxd, J$_1$=11, J$_2$=7Hz, 1H); 4.03(m, 1H); 4.20(dxd, J$_1$=11, J$_2$=4Hz, 1H) δppm.
NMR ($^{13}$C, 360MHz, CDCl$_3$): 16.5(q); 21.0(q); 21.2(t); 21.4(q); 28.0(d); 31.1(t); 33.0(d); 39.2(t); 43.3(t); 68.3(t); 70.2(d); 171.5(s) δppm.
MS: 171(1), 154(9), 136(15), 121(13), 112(58), 97(52), 81(57), 69(58), 55(53), 43(100).

Jones reagent was added dropwise to a solution of 7.44 g (34.8 mmole) of the above-mentioned acetate in acetone (100 ml) until the oxidation, followed by thin layer chromatography, was complete. The reaction mixture was filtered on Celite® and evaporated, extracted with ether and the ether solution washed three times with water. Evaporation of the ether gave 7.29 g (yield 99%) (1R,4R,8S)-3-oxo-9-p-menthanyl acetate having the following characteristics:
NMR($^1$H, 360MHz, benzène): 0.70(d, J=7Hz, 3H); 0.87(d, J=7Hz, 3H); 1.15(m, 1H); 1.31(m, 1H); 1.43(m, 1H); 1.54(m, 1H); 1.72(m, 1H); 1.72(s, 3H); 1.87(dxd, J$_1$=13, J$_2$=8Hz, 1H); 2.03(m, 2H); 2.11(dxd, J$_1$=13, J$_2$=5Hz, 1H); 3.93(dxd, J$_1$=10, J$_2$=5Hz, 1H); 4.02(dxd, J$_1$=10, J$_2$=4Hz, 1H) δppm.
NMR($^{13}$C, 360MHz, CDCl$_3$): 15.5(q); 20.6(q); 20.9(q); 26.3(t); 29.9(t); 31.6(d); 33.4(d); 48.3(t); 52.7(d); 66.8(t); 171.1 (s); 212.6(s) δppm.
MS: 212(1, M$^+$), 169(1), 152(6), 137(11), 123(8), 112(100), 97(17), 69(29), 43(33).

2.9G of lithium (415 mmole) were added in small portions, at −60° C. and over 2 h, to a solution containing 5.78 g (27.3 mmole) of the acetate prepared above, 33 g (620 mmole) of ammonium chloride in 300 ml of liquid $NH_3$ and 100 ml of ether. The liquid $NH_3$ was evaporated and 100 ml of ether and 100 ml of water added. The organic phase was extracted with brine to give 4.7 g of raw product. Purification by flash chromatography of the latter (eluting agent: pentane/ether =1/2) gave (+)(1R,3S,4R,8S)-3,9-p-menthanediol, with the following characteristics:

$[\alpha]_D^{20}$=+8.7°; c = 1.9%, in $CHCl_3$
NMR($^1H$, 360MHz, $CDCl_3$): 0.95(d, J=7Hz, 3H); 0.98(d, l=7Hz, 3H); 1.33– 1.51(m, 6H); 1.78(m, 2H); 2.07(m, 1H); 3.57(dxd, $J_1$=11, $J_2$=4Hz, 1H); 3.65(dxd, $J_1$=11, $J_2$=5Hz, 1H); 3.70(dxdxd, $J_1$=9, $J_2$=4, $J_3$=4Hz, 1H) δppm.
NMR($^{13}C$, 360MHz, $CDCl_3$): 12.4(q); 18.7(q); 24.3(t); 28.1(d); 31.1(t); 38.4(d); 41.0(t); 48.8(d); 66.3(d); 66.9(t) δppm.
MS: 154(6), 137(11), 123(25), 95(55), 81(100), 67(60), 55(65), 41(45).

3.09G (18 mmole) of this diol, in solution in 8 ml of ethyl acetate, were added to 6.92 g (44 mmole) of potassium permanganate in 25 ml of ethyl acetate. The reaction mixture was stirred overnight at room temperature and then hydrolized by adding a solution of sodium bisulfite until complete discoloring. The white precipitate was filtered and the organic phase was washed with brine until pH 7. After drying and concentrating, there were obtained 1.97 g of (−)(3S,3aR,6R,7aS)-perhydro-3,6-dimethyl-2-benzo[b]furanone 95% pure. The analytical characters of this furanone are presented hereafter:

$[\alpha]_D^{20}$=−71.7°; c=0.8%, in $CHCl_3$
IR: 2943, 1807, 1186, 989 $cm^{-1}$
NMR($^1H$, 360MHz, $CDCl_3$): 1.07(d, J=7Hz, 3H); 1.17(d, J=7Hz, 3H); 1.4– 1.7(m, 4H); 1.72(dxd, $J_1$=12, $J_2$=5Hz, 1H); 1.94(m, 1H); 2.10(dxdxd, $J_1$=12, $J_2$=3, $J_3$=3Hz, 1H); 2.30(m, 1H); 2.65(dxq, $J_1$=7, $J_2$=7Hz, 1H); 4.23(dxdxd, $J_1$=12, $J_2$=12, $J_3$=4Hz, 1H) δppm.
NMR($^{13}C$, 360MHz, $CDCl_3$): 9.6(q); 19.2(q); 20.2(t); 28.1(d); 31.0(t); 36.1 (t); 38.9(d); 48.1 (d); 78.2(d); 180.3(s) δppm.
MS: 167(1), 124(3), 109(15), 95(22), 81(100), 67 (57), 55(20), 41(15).
Odor: described in the introduction.

F. Preparation of (−)-(3R,3aR,6R,7aS)-perhydro-3,6-dimethyl-2-benzo[b] furanone

A solution of 0.33 g (2 mmole) of the furanone obtained under E and 0.064 g (1.2 mmole) of anhydrous sodium methylate in THF (6 ml) was stirred for 4 h at room temperature. The reaction was quenched with a 10% HCl solution and the reaction mixture extracted with ether. The organic phase was washed with brine, dried and concentrated to obtain a mixture of lactones. The desired furanone was separated from this mixture by preparative gas chromatography.

$[\alpha]_D^{20}$=−9.8°; c=0.92%, in $CHCl_3$
IR: 2940, 1809, 1171, 999 $cm^{-1}$
NMR($^1H$, 360MHz, $CDCl_3$): 1.07(d, J=7Hz, 3H); 1.23(d, J=7Hz, 3H); 1.48(m, 2H); 1.62(m, 2H); 1.70(dxd, $J_1$=12, $J_2$=5Hz, 1H); 1.80(m, 1H); 2.16(dxdxd, $J_1$=12, $J_2$=3, $J_3$=3Hz, 1H); 2.30(m, 2H); 3.99 (dxdxd, $J_1$=11, $J_2$=9, $J_3$=4Hz, 1H) δppm.
NMR($^{13}C$, 360MHz, $CDCl_3$): 12.5(q); 19.2(q); 23.0(t); 28.2(d); 31.1(t); 35.7(t); 41.5(d); 52.5(d); 79.3(d); 179.5(s) δppm.
MS: 147(1), 140(2), 133(1), 124(3), 109(12), 95 (22), 81(100), 67(52), 55(23), 41(18).
Odor: coumarinic, flouve, hay, sulfur, rubbery.

G. Preparation of (+)-(3aS,6R,7aR)-perhydro-6-methyl-3-methylene-2-benzo [b]furanone and of (3aS,6R,7aS)-perhydro-6-methyl-3-methylene-2-benzo [b]furanone These two lactones, prepared according to Scheme I, or as described in the previously cited prior art, had the following characteristics:
(+)-(3aS, 6R, 7aR)-perhydro-6-methyl-3-methylene-2-benzo[b]furanone
$[\alpha]_D^{20}$=+55.22°
NMR($^1H$, 360MHz, $CDCl_3$): 1.04(d, J=6Hz, 3H); 1.05–1.20(m, 1H); 1.25–1.45(m, 2H); 1.64(m, 1H); 1.84(dxm, J=14Hz, 1H); 2.13(dxm, J=14Hz, 1H); 2.26(dxdxd, $J_1$=13, $J_2$=2, $J_3$=2Hz, 1H); 2.37(m, 1H); 3.73(dxdxd, $J_1$=12, $J_2$=12, $J_3$=4Hz, 1H); 5.40(d, J=4Hz, 1H); 6.07(d, J=4Hz, 1H) δppm.
NMR($^{13}C$, 360MHz, $CDCl_3$): 22.0(q); 25.0(t); 31.4(d); 33.8(t); 38.6(t); 48.7(d); 82.6(d); 116.9(t); 139.8(s); 170.7(s) δppm.
MS: 166(4, $M^+$), 138(40), 109(36), 94(100), 81(73), 67(65), 55(47), 41(25).
Odor: coumarinic, lactonic, tonka, daffodil, very powerful.
(3aS, 6R, 7aS)-perhydro-6-methyl-3-methylene-2-benzo[b] furanone
NMR($^1H$, 360MHz, $CDCl_3$): 0.94(d, J=6Hz, 3H); 1.00(m, 1H); 1.25–1.40(m, 2H); 1.45–1.70(m, 2H); 1.85(m, 1H); 2.20(dxm, J=14Hz, 1H); 2.84(m, 1H); 2.52(m, 1H); 5.54(d, J=1Hz, 1H); 6.10(d, J=1Hz, 1H) δppm
NMR($^{13}C$, 360MHz, $CDCl_3$): 21.7(q); 25.6(d); 28.3(t); 31.2(t); 35.8(t); 39.5(d); 77.2(d); 119.5(t); 142.4(s); 170.9(s) δppm.
Odor: coumarinic, lactonic, tonka.

H. Preparation of (−)-(3aS,6R,7aS)-perhydro-3,3,6-trimethyl-2-benzo[b] furanone 2.54G (35.8 mmole) of pyrrolidine were charged into a flask at −40°, then 14.3 ml of butyllithium 2.5M in hexane added thereto. The temperature was allowed to increase to 0° then cooled again to −40° and 5 g (29.8 mmole) of perhydro-3,6-dimethyl-2-benzo[b]furanone (mixture of 4 diastereomers) added to the reaction. The temperature was allowed to increase to 0° and then 12.8 g (90.3 mmole) of methyl iodide added before returning to room temperature. After 1 h, the reaction mixture was hydrolized and extracted with ether. The organic phase was washed with water, dried over $MgSO_4$ concentrated. The raw product was chromatographed on silica (eluting agent: $Et_2O$/pentane=3/7) to give thus the desired lactone (yield ~10%).

$[\alpha]_D^{20}$=−35.5°; c=0.65% in $CHCl_3$
NMR($^1H$, 360MHz, $CDCl_3$): 0.8–0.95(m, 1H); 0.92(d, J=7Hz, 3H); 1.16(s, 3H); 1.29(s, 3H); 1.1–1.25(m, 2H); 1.53(m, 1H); 1.62–1.75(m, 2H); 1.88(m, 1H); 2.24(m, 1H); 4.69(m, 1H) δppm.
NMR($^{13}C$, 360MHz, $CDCl_3$): 19.16(q); 21.93(q); 23.27(q); 24.89(t); 26.27(d); 32.32(t); 36.41(t); 44.80(d); 45.66(s); 76.21(d); 182.11(s) δppm.
MS: 182(12), 132(2), 123(24), 95(100), 81(87), 67(38), 19(55), 41(7).
Odor: lactonic, fruity, coumarinic.

The following enantiomers of the furanones described under sections A to F presented the properties cited hereafter:
(3S, 3aR, 6S, 7aS)-perhydro-3,6-dimethyl-2-benzo[b]furanone
(87% pure)
Odor: butyric, rancid, coumarinic, lactonic, sulfury, powerful.
(+)-(3R, 3aR, 6S, 7aR)-perhydro-3,6-dimethyl-2-benzo[b] furanone
$[\alpha]_D^{20}$=+69,9°
Odor: coumarinic, hay, earthy, lactonic.
(+)-(3R, 3aR, 6S, 7aR)-perhydro-3,6-dimethyl-2-benzo[b]

furanone
[α]$_D^{20}$=+45,8°
Odor: coumarinic, walnut, walnut oil.

(3S,3aS,6S,7aR)-Perhydro-3,6-dimethyl-2-benzo[b]furanone, (3S,3aS,6S,7aS)-perhydro-3,6-dimethyl-2-benzo[b]furanone, (3R,3aR,6S,7aS)-perhydro-3,6-dimethyl-2-benzo[b]furanone and (3R,3aS,6S,7aR)-perhydro-3,6-dimethyl-2-benzo[b]furanone were also prepared.

The perfumery applications according to the invention are now described in greater detail by way of the following examples.

EXAMPLE 1

Preparation of a perfuming composition

A base perfuming composition, intended for a masculine, oriental type perfume, was prepared by admixing the following ingredients:

| Ingredients | Parts by weight |
|---|---|
| Linalyl acetate | 210 |
| 10%* Ambrox ® DL[1] | 350 |
| Methyl anthranilate dist. | 25 |
| 10%* 4-(4-Hydroxyphenyl)-2-butanone | 15 |
| Synth. bergamot oil. | 135 |
| 10%* Ceylan cinnamon oil | 70 |
| 10%* Eugenol | 40 |
| Lemon essential oil | 110 |
| Heliotropine ord. | 120 |
| Hydroxycitronellal | 35 |
| 10%* Indol purif. | 15 |
| Polywood ®[2] | 190 |
| Dihydromyrcenol[3] | 180 |
| Linalol | 50 |
| Lyral ®[4] | 400 |
| Synth. tangerine oil | 30 |
| Iralia ®[5] | 90 |
| Methylnaphtylketone cryst. | 20 |
| Methyl jasmonate | 300 |
| Patchouli essential oil | 120 |
| Sandalore ®[6] | 50 |
| Tonalid ®[7] | 500 |
| Exaltolide ®[8] | 200 |
| Vanillin | 95 |
| Vertofix coeur[9] | 250 |
| TOTAL | 3600 |

*in dipropyleneglycol
[1] tetramethyl perhydronaphtofurane, origin: Firmenich SA, Geneva, Switzerland
[2] perhydro-5,5,8a-trimethyl-2-naphthyl acetate; origin: Firmenich SA, Geneva, Switzerland
[3] origin: International Flavors and Fragrances Inc., U.S.A.
[4] 4-(4-hydroxy-4-methylpentyl)-3-cyclohexene-1-carboxaldehyde; origin: International Flavors and Fragrances Inc., U.S.A.
[5] methylionone; origin: Firmenich SA, Geneva, Switzerland
[6] 5-(2,2,3-trimethylcyclopent-3-enyl)-3-methylpentan-2-ol; origin: L. Givaudan, Vernier, Switzerland
[7] 7-acetyl-1,1,3,4,4,6-hexamethyltetraline; origin: PFW, Hollande
[8] pentadecanolide; origin: Firmenich SA, Geneva, Switzerland
[9] origin: International Flavors and Fragrances Inc., U.S.A.

To this base composition of the balsamic-floral, woody, musky type, there were added 400 parts by weight of coumarine to obtain a composition A, respectively 400 parts by weight of perhydro-3,6-dimethyl-2-benzo[b]furanone to obtain a novel composition B.

These two compositions A and B were compared on a blind test by a panel of expert perfumers. According to the latter, novel composition B developed a far more balsamic odor than composition A, an odor which was reminiscent of tonka beans. Furthermore, the floral character of composition B seemed completely stifled at this concentration of furanone.

Upon reduction by half of the amount of perhydro-3,6-dimethyl-2-benzo[b]furanone added to the base composition, there was obtained a novel composition, the odor of which was much closer t6 that of composition A, albeit with a less vanilla character.

When 100 parts by weight of perhydro-3,6-dimethyl-2-benzo[b]furanone were added to the base composition, there was obtained a fragrance effect which was even more similar to that which could be obtained with 400 parts by weight of coumarine, i.e. a novel composition was obtained, the odor of which was very dose to that of composition A, although altogether more woody and less vanilla-like.

The fragrance performance of this furanone was also compared with that of its unsaturated homologue, 5,6,7,7a-tetrahydro-7a-methoxy-3,6-dimethyl- 2(4H)-benzo[b]furanone or mintlactone.

When 200 parts by weight of the furanone according to the present invention and 200 parts by weight of mintlactone were added to two distinct samples of the above-mentioned base composition, there were obtained two compositions, respectively C and D, which possessed completely different odors. While the odor of novel composition C, containing perhydro-3,6-dimethyl-2-benzo[b]furanone, had as dominant character the oriental, vanilla-coumarinic note, that of composition D, which contained mintlactone, was vaguely powdery-vanilla, with a "food" type character, the vanilla note actually stifling all the fragrance of composition D. Unlike the latter, composition C had a dearly perfumery-like, rich odor, with a lot more volume and an elegant note of the oriental-coumarinic type.

On the other hand, composition D seemed much less "concentrated" than composition C.

EXAMPLE 2

Test of substantivity on cloth

There were prepared samples of a perfumed fabric softener base by adding to distinct samples of a standard, non-perfumed, fabric softener, respectively perhydro-3,6-dimethyl-2-benzo[b]furanone, coumarine, 8-oxatricydo[5.3.1.0$^{2,6}$] undecan-9-one (origin: Firmenich SA; see U.S. Pat. No. 3,981,892), cis-10,10-dimethyl-tricyclo [7.1.1.0$^{2,7}$] undec-2-en-4-one (origin: Firmenich SA; see U.S. Pat. No. 4,226,745), 1-oxaspiro[4.5]decan-2-one (origin: Firmenich SA; see U.S. Pat. No. 5,057,239), and mintlactone, in the amounts indicated in the following table (parts by weight).

TABLE

| Ingredients | Sample 1 | 2 | 3 | 4 | 5 | 6 |
|---|---|---|---|---|---|---|
| non-perfumed fabric softener | 99.9 | 99.9 | 99.9 | 99.9 | 99.9 | 99.9 |
| perhydro-3,6-dimethyl-2-benzo[b]furanone | 0.1 | — | — | — | — | — |
| coumarine | — | 0.1 | — | — | — | — |
| 8-oxatricyclo[5.3.1.0$^{2,6}$]undecan-9-one | — | — | 0.1 | — | — | — |
| cis-10,10-dimethyl-tricyclo[7.1.1.0$^{2,7}$]undec-2-en-4-one | — | — | — | 0.1 | — | — |
| 1-oxaspiro[4.5]decan-2-one | — | — | — | — | 0.1 | — |
| mintlactone | — | — | — | — | — | 0.1 |

Six standard batches of textiles, containing cotton, acrylic fiber and nylon textiles, were treated separately in six washing machines with samples 1 to 6 prepared as indicated above. The six batches of textiles thus treated were then evaluated on a blind test by a panel of expert perfumers, both wet and after being dried.

The results of these comparative essays showed that, in the opinion of the perfumers, the batch of textiles treated with sample 1, which contained perhydro-3,6-dimethyl-2-benzo[b]furanone, developed an odor which was judged five to ten times stronger than the odor of the textiles treated with sample 2, containing coumarine, and this both on the wet and dried textiles. The odor of the batch treated with sample 1 also lingered for much longer on the textiles after drying.

The textiles treated with sample 3 developed an odor which was judged less powerful and substantive than that of the textiles treated with sample 2, while the odor of the batch treated with sample 4 was more powerful and tenacious than that of the latter, and the odor of the textiles washed with sample 5 was comparable, in intensity and durability, to the odor of the textiles treated with sample 2. It was the unanimous opinion of the perfumers that all these three batches of textiles, treated with samples 3, 4 and 5, possessed odors which were clearly inferior, in strength and substantivity, to the odor of the batch treated with sample 1, and this both when taken out of the washing machine and after the drying of the textiles.

Furthermore, the textiles treated with sample 6, when wet, developped an odor which was much weaker than that of the textiles treated with sample 1, an odor which also disappeared very quickly from the dried textiles. This batch of textiles was in fact the least substantive of all the batches mentioned above.

I claim:

1. A method of conferring, improving, enhancing or modifying the odor of a perfuming composition or a perfumed article, which method comprises adding to said composition or article a fragrance effective amount of a furanone of formula

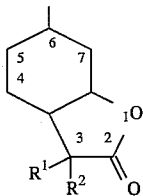

(I)

wherein symbols $R^1$ and $R^2$, taken separately, are identical and represent each a methyl radical, or are different and represent each a hydrogen atom or a methyl radical, or, taken together, represent a methylene radical.

2. A method according to claim 1, which further comprises adding said furanone in the form of one of its optically active isomers.

3. A method according to claim 2, wherein the isomer is (+)-(3aS,6R,7aR)-perhydro-6-methyl-3-methylene-2-benzo[b]furanone or (−)-(3aS,6R,7aS)-perhydro-(3,3,6)-trimethyl-2-benzo[b]furanone.

4. A method according to claim 2, which comprises adding perhydro-3,6-dimethyl-2-benzo[b]furanone in the form of one of the following isomers:

a) (+)-(3R,3aS,6R,7aR)-perhydro-3,6-dimethyl-2-benzo[b]furanone, b) (+)-(3S,3aS,6R,7aR)-perhydro-3,6-dimethyl-2-benzo[b]furanone, or c) (−)-(3S,3aR,6R,7aS)-perhydro-3,6-dimethyl-2-benzo[b]furanone.

5. A method according to claim 1, which comprises adding perhydro-3,6-dimethyl-2-benzo[b]furanone in the form of a mixture of at least two of its optically active isomers.

6. A method according to claim 5, wherein the combined weight of (+)-(3R,3aS,6R,7aR)-perhydro-3,6-dimethyl-2-benzo[b]furanone and (+)-(3S,3aS,6R,7aR)-perhydro-3,6-dimethyl-2-benzo[b]furanone in said mixture is about 50% or more.

7. A method according to claim 5 wherein said mixture contains about 50% by weight of (+)-(3S,3aS,6R,7aR)-perhydro-3,6-dimethyl-2-benzo[b]furanone, about 30% by weight of (+)-(3R,3aS,6R,7aR)-perhydro-3,6-dimethyl-2-benzo[b]furanone, about 11% by weight of (−)-(3S,3aS,6R,7aS)-perhydro-3,6-dimethyl-2-benzo[b]furanone and about 7% by weight of (−)-(3R,3aS,6R,7aS)-perhydro-3,6-dimethyl-2-benzo[b]furanone, relative to the weight of the mixture.

8. A method according to claim 5, wherein said mixture contains about 50% or more of one of:

a) (+)-(3R,3aS,6R,7aR)-perhydro-3,6-dimethyl-2-benzo[b]furanone; or b) (+)-(3S,3aS,6R,7aR)-perhydro-3,6-dimethyl-2-benzo[b]furanone.

9. A perfuming composition or a perfumed article resulting from the method according to claim 1 or 5.

10. A perfumed article according to claim 9, in the form of a perfume or a cologne, a soap, a bath or shower gel, a shampoo or other hair-care product, a cosmetic preparation, a body or air deodorant, a detergent or a fabric softener, or a household product.

11. A perfuming composition containing about 50% or more of:

a) (+)-(3S, 3aS, 6R, 7aR)-perhydro-3,6-dimethyl-2-benzo[b]furanone; or b) (+)-(3R,3aS,6R,7aR)-perhydro-3,6-dimethyl-2benzo[b]furanone: together with a solvent or adjuvant.

12. The perfuming composition of claim 11, wherein at least 50% of its weight is formed of a mixture of (+)-(3S, 3aS,6R,7aR)-perhydro-3,6-dimethyl- 2-benzo[b]furanone and (+)-(3R,3aS,6R,7aR)-perhydro- 3,6-dimethyl-2-benzo[b]furanone.

13. A perfuming composition according to claim 12, containing about 50% by weight of (+)-(3S,3aS,6R,7aR)-perhydro-3,6-dimethyl-2-benzo[b]furanone, about 30% by weight of (+)-(3R,3aS,6R,7aR)-perhydro-3,6-dimethyl-2-benzo[b]furanone, about 11% by weight of (−)-(3S,3aS,6R,7aS)-perhydro-3,6-dimethyl-2-benzo[b]furanone and about 7% by weight of (−)-(3R,3aS,6R,7aS)-perhydro-3,6-dimethyl- 2-benzo[b]furanone, relative to the weight of the composition.

14. A method for reconstituting the odor characteristic of coumarine in a perfuming composition or a perfumed article, which method comprises adding to said composition or article a fragrance effective amount of a furanone of formula (I) as defined in claim 1.

15. A method according to claim 14, which comprises adding said furanone in the form of a mixture of at least two of its optically active isomers.

16. A perfuming composition containing perhydro-3,6-dimethyl-2-benzo[b]furanone in the form of one of the following isomers:

(a) (+)-(3R, 3aS, 6R, 7aR)-perhydro-3,6-dimethyl-2-benzo[b]furanone (b) (+)-(3S, 3aS, 6R, 7aR)-perhydro-3,6-dimethyl-2-benzo[b]furanone (c) (−)-(3S, 3aR, 6R, 7aS)-perhydro-3,6-dimethyl-2-benzo[b]furanone.

17. The method according to claim 1, wherein the furanone is present in an amount sufficient to provide a coumarinic character which is rich in aromatic tonka and flouve notes.

18. The product according to claim 10, wherein the furanone is present in an amount sufficient to provide a coumarinic character which is rich in aromatic tonka and flouve notes.

19. A perfuming composition or perfumed article comprising a composition or article and the composition of claim 11, wherein the furanone is present in an amount sufficient to provide a coumarinic character which is rich in aromatic tonka and flouve notes.

20. A perfuming composition or perfumed article comprising a composition or article and the composition of claim 16, wherein the furanone is present in an amount sufficient to provide a coumarinic character which is rich in aromatic tonka and flouve notes.

* * * * *